(12) United States Patent
Kim

(10) Patent No.: US 10,405,842 B2
(45) Date of Patent: Sep. 10, 2019

(54) RETRACTION SYSTEM AND METHOD OF USE

(71) Applicant: K2M, Inc., Leesburg, VA (US)

(72) Inventor: Choll Kim, San Diego, CA (US)

(73) Assignee: K2M, Inc., Leesburg, VA (US)

( * ) Notice: Subject to any disclaimer, the term of this patent is extended or adjusted under 35 U.S.C. 154(b) by 39 days.

(21) Appl. No.: 15/715,613

(22) Filed: Sep. 26, 2017

(65) Prior Publication Data

US 2018/0085105 A1 Mar. 29, 2018

Related U.S. Application Data

(60) Provisional application No. 62/399,520, filed on Sep. 26, 2016.

(51) Int. Cl.
| | |
|---|---|
| *A61B 17/88* | (2006.01) |
| *A61B 17/02* | (2006.01) |
| *A61F 2/44* | (2006.01) |
| *A61B 17/16* | (2006.01) |
| *A61B 17/17* | (2006.01) |
| *A61B 17/00* | (2006.01) |
| *A61F 2/46* | (2006.01) |

(52) U.S. Cl.
CPC ........ *A61B 17/025* (2013.01); *A61B 17/0206* (2013.01); *A61F 2/442* (2013.01); *A61B 17/1671* (2013.01); *A61B 17/1757* (2013.01); *A61B 17/8897* (2013.01); *A61B 2017/00473* (2013.01); *A61B 2017/0256* (2013.01); *A61F 2/4611* (2013.01)

(58) Field of Classification Search
CPC .............. A61B 17/025; A61B 17/0206; A61B 17/1671; A61B 17/1757; A61B 17/8897; A61B 2017/00473; A61B 2017/0256; A61F 2/442; A61F 2/4611
USPC ....... 600/210, 213, 215, 222, 224, 231, 232; 606/246, 279, 80, 84, 85, 87, 90, 96, 105; 623/17.11, 17.16
See application file for complete search history.

(56) References Cited

U.S. PATENT DOCUMENTS

| | | |
|---|---|---|
| 3,749,088 A | 7/1973 | Kohlmann |
| 5,484,437 A | 1/1996 | Michelson |
| 5,728,046 A | 3/1998 | Mayer et al. |
| 5,813,978 A | 9/1998 | Jako |

(Continued)

FOREIGN PATENT DOCUMENTS

| | | |
|---|---|---|
| EP | 1611851 A1 | 1/2006 |
| WO | 2010114625 A2 | 10/2010 |

*Primary Examiner* — Pedro Philogene
*Assistant Examiner* — David C Comstock
(74) *Attorney, Agent, or Firm* — Lerner, David, Littenberg, Krumholz & Mentlik, LLP

(57) ABSTRACT

A method of distracting adjacent vertebral bodies includes inserting a first pin into a first vertebral body, inserting a second pin into a second vertebral body adjacent the first vertebral body, positioning a first retractor blade over the first pin, positioning a second retractor blade over the second pin, attaching a first arm of a frame to the first retractor blade and a second arm of the frame to the second retractor blade, displacing the second arm of the frame away from the first arm to distract the first and second vertebral bodies, inserting prongs of a lateral protector into respective channels defined in the first and second retractor blades, and retracting tissue by a transverse blade of the lateral protector.

30 Claims, 16 Drawing Sheets

(56) References Cited

U.S. PATENT DOCUMENTS

| | | | |
|---|---|---|---|
| 5,928,139 A | 7/1999 | Koros et al. | |
| 5,944,658 A | 8/1999 | Koros et al. | |
| 6,004,326 A * | 12/1999 | Castro | A61B 17/025 606/99 |
| 6,175,758 B1 * | 1/2001 | Kambin | A61B 17/1757 600/426 |
| 6,436,119 B1 | 8/2002 | Erb et al. | |
| 6,716,218 B2 | 4/2004 | Holmes et al. | |
| 7,494,463 B2 | 2/2009 | Nehls | |
| 7,615,079 B2 | 11/2009 | Flickinger et al. | |
| 7,666,201 B2 | 2/2010 | Grayzel et al. | |
| 7,846,093 B2 | 12/2010 | Gorek et al. | |
| 8,241,294 B2 | 8/2012 | Sommerich et al. | |
| 8,377,070 B2 | 2/2013 | Gauthier | |
| 8,449,463 B2 | 5/2013 | Nunley et al. | |
| 8,636,657 B2 | 1/2014 | Hamada | |
| 8,974,381 B1 * | 3/2015 | Lovell | A61B 17/0206 600/232 |
| 9,017,409 B2 | 4/2015 | Wallenstein et al. | |
| 9,028,522 B1 * | 5/2015 | Prado | A61B 17/025 606/191 |
| 9,782,158 B2 | 10/2017 | Nunley et al. | |
| 2001/0049527 A1 | 12/2001 | Cragg | |
| 2003/0149341 A1 | 8/2003 | Clifton | |
| 2004/0010312 A1 | 1/2004 | Enayati | |
| 2004/0230191 A1 | 11/2004 | Frey et al. | |
| 2005/0149035 A1 | 7/2005 | Pimenta et al. | |
| 2005/0216088 A1 | 9/2005 | McKinley et al. | |
| 2006/0084844 A1 | 4/2006 | Nehls | |
| 2006/0247645 A1 | 11/2006 | Wilcox et al. | |
| 2006/0287730 A1 | 12/2006 | Segal et al. | |
| 2008/0021284 A1 | 1/2008 | Hestad et al. | |
| 2008/0183046 A1 | 7/2008 | Boucher et al. | |
| 2008/0262501 A1 | 10/2008 | Chen et al. | |
| 2009/0036746 A1 | 2/2009 | Blackwell et al. | |
| 2009/0043340 A1 * | 2/2009 | Lowry | A61B 17/7059 606/280 |
| 2009/0228110 A1 | 9/2009 | McClintock | |
| 2010/0130827 A1 | 5/2010 | Pimenta et al. | |
| 2010/0174146 A1 | 7/2010 | Miles et al. | |
| 2011/0034777 A1 | 2/2011 | Ames et al. | |
| 2014/0031874 A1 * | 1/2014 | Kucharzyk | A61B 17/7076 606/279 |
| 2016/0106408 A1 * | 4/2016 | Ponmudi | A61B 17/025 606/90 |
| 2016/0345952 A1 * | 12/2016 | Kucharzyk | A61B 17/0206 |

* cited by examiner

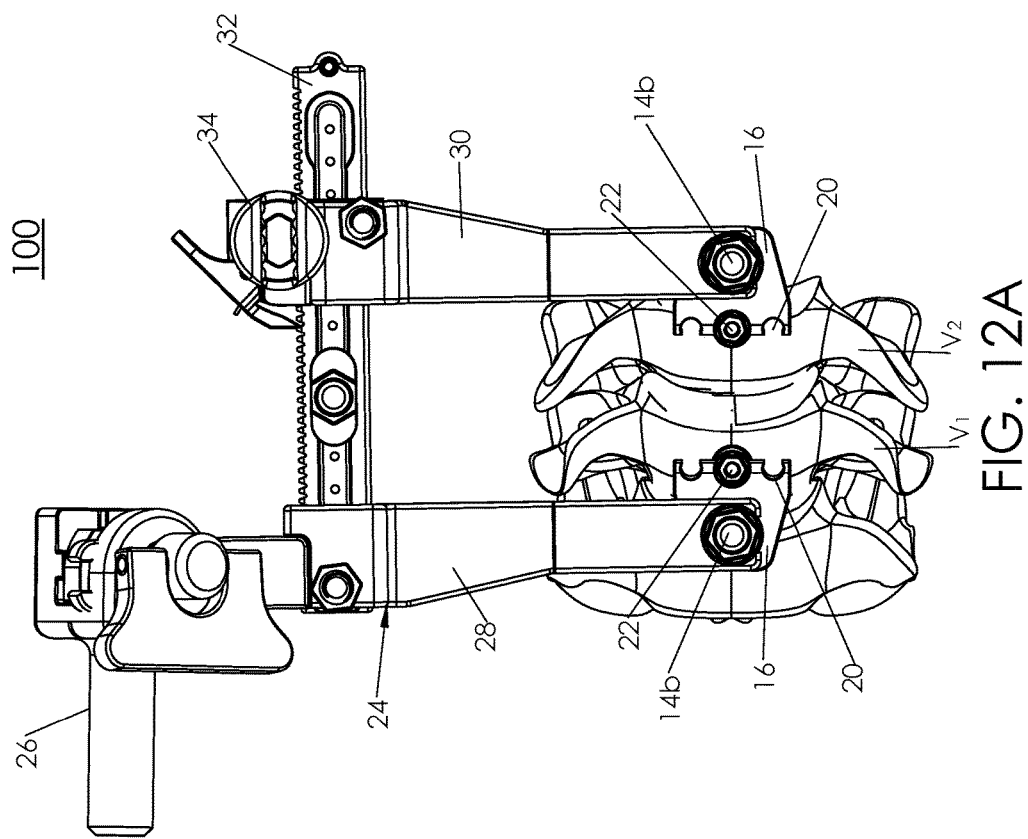

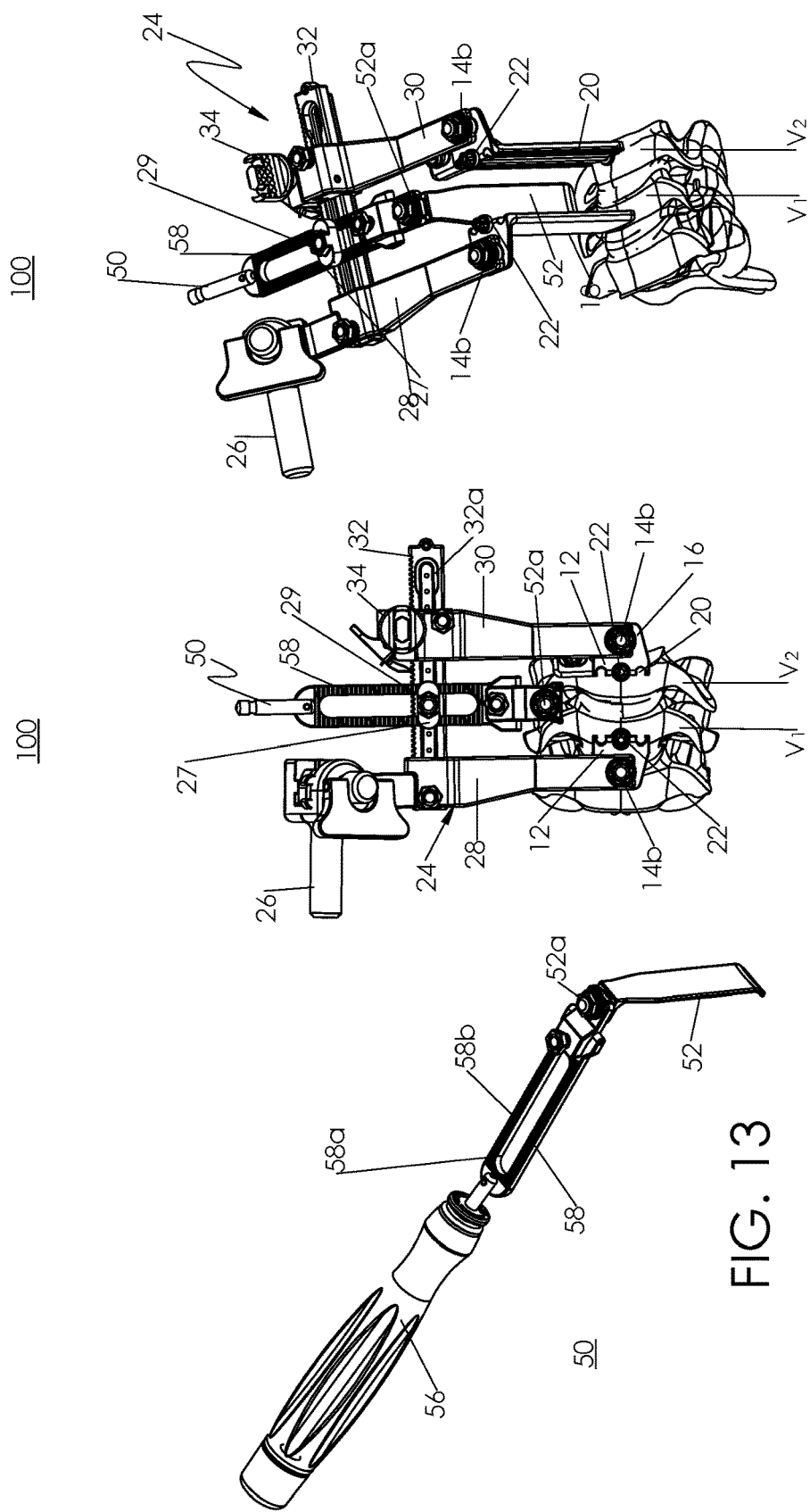

RETRACTION SYSTEM AND METHOD OF USE

CROSS-REFERENCE TO RELATED APPLICATION

This application claims priority to, and the benefit of, U.S. Provisional Patent Application Ser. No. 62/399,520, filed on Sep. 26, 2016, the entire contents of which are incorporated by reference herein.

BACKGROUND

1. Technical Field

The present disclosure relates to an instrument for spinal surgery and, more particularly, to an instrument and a method for distracting vertebral bodies.

2. Discussion of Related Art

The spine is a flexible structure capable of a large range of motion. There are various disorders, diseases and types of injury, which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function.

Disease, the effects of aging, or physical trauma resulting in damage to the spine has been treated in many instances by fixation or stabilization of the effected vertebra. A wide variety of spinal fixation apparatuses have been employed in surgical procedures for correcting spinal injuries and the effects of spinal diseases. When the disc has degenerated to the point of requiring removal, a partial or complete discectomy may be performed.

After a partial or complete discectomy, the normally occupied space between adjacent vertebral bodies is subject to collapse and/or misalignment due to the absence of all or a part of the intervertebral disc. In such situations, the physician may insert one or more prosthetic spacers between the affected vertebral bodies to maintain normal disc spacing and/or the normal amount of lordosis in the affected region.

Therefore, a continuing need exists for an improved instrument and a method for distracting vertebral bodies.

SUMMARY

In accordance with an embodiment of the present disclosure, there is provided a method of distracting adjacent vertebral bodies. The method includes inserting a first pin into a first vertebral body, inserting a second pin into a second vertebral body adjacent the first vertebral body, positioning a first retractor blade over the first pin, positioning a second retractor blade over the second pin, attaching a first arm of a frame to the first retractor blade and a second arm of the frame to the second retractor blade, displacing the second arm of the frame away from the first arm to distract the first and second vertebral bodies, inserting prongs of a lateral protector into respective channels defined in the first and second retractor blades, and retracting tissue by a transverse blade of the lateral protector.

In an embodiment, the method may further include inserting an indicator pin in the center of a vertebral disc space.

In another embodiment, inserting the indicator pin may include inserting the indicator pin in the center point in a medial-lateral direction.

In yet another embodiment, inserting the indicator pin may further include inserting the indicator pin in the center point in a cephalad-caudal direction.

In yet another embodiment, the method may further include inserting a reamer over the indicator pin to remove osteophytes from the vertebral body using a cutting surface at a distal end of the reamer.

In still yet another embodiment, the method may further include inserting a drill guide through the indicator pin such that the drill guide is in registration with the first and second vertebral bodies.

In an embodiment, the method may further include drilling holes in the first and second vertebral bodies through first and second bores of the drill guide in registration with the first and second vertebral bodies.

In an embodiment, positioning the first retractor blade over the first pin may include sliding the first pin through a longitudinal channel defined in the first retractor blade.

In another embodiment, the method may further include clearing a disc space located between the first and second vertebral bodies.

In yet another embodiment, the method may further include implanting a device into the cleared disc space.

In still yet another embodiment, the method may further include displacing the second arm of the frame towards the first arm such that the first and second vertebral bodies engage the device disposed in the cleared disc space.

In an embodiment, the method may further include attaching a medial blade to the frame to retract tissue in the area around the first and second retractor blades.

In another embodiment, the method may further include detaching the second arm of the frame from the second retractor.

In an embodiment, the method may further include inserting a third pin into a third vertebral body adjacent the first vertebral body.

In another embodiment, the method may further include rotating the first retractor blade about 180 degrees about the first pin.

In yet another embodiment, the method may further include attaching the second retractor blade over the third pin and attaching the second arm of the frame to the second retractor blade.

In still yet another embodiment, the method may further include displacing the second arm of the frame away from the first arm to distract the first and third vertebral bodies.

In still yet another embodiment, the method may further include clearing a disc space located between the first and third vertebral bodies.

In still yet another embodiment, the method may further include implanting a device into the cleared disc space between the first and third vertebral bodies.

In still yet another embodiment, the method may further include displacing the second arm of the frame towards the first arm such that the first and third vertebral bodies engage the device disposed in the cleared disc space between the first and third vertebral bodies.

In an embodiment, the method may further include disengaging the prongs of the lateral protector from the first and second retractor blades.

In accordance with another embodiment of the present disclosure, there is provided a method of distracting adjacent vertebral bodies. The method includes inserting first and second pins into respective first and second vertebral bodies and positioning first and second retractor blades of a retractor system over the respective first and second pins. In particular, the retractor system includes a frame including a first arm, a second arm movable relative to the first arm, and a third arm operatively supporting the first and second arms; and a lateral protector including prongs configured to be received in respective channels defined in the first and second retractor blades, and a transverse blade. The first and second retractor blades are coupled to the respective first and second arms of the frame. The method further includes displacing the second arm of the frame away from the first arm to distract the first and second vertebral bodies; inserting the prongs of the lateral protector into the respective channels of the first and second retractor blades; and retracting tissue by the transverse blade of the lateral protector.

BRIEF DESCRIPTION OF THE DRAWINGS

The above and other aspects and features of the present disclosure will become more apparent in light of the following detailed description when taken in conjunction with the accompanying drawings in which:

FIG. 12A is a top view of the frame of the retractor system of FIG. 1, including a mounting arm;

FIG. 13 is a perspective view of a medial retractor of the retractor system of FIG. 1;

FIG. 14 is a top view of the retractor system of FIG. 1 illustrating use with the medial retractor of FIG. 13;

FIG. 15 is a perspective view of the retractor system of FIG. 14;

DETAILED DESCRIPTION

Figure 1:
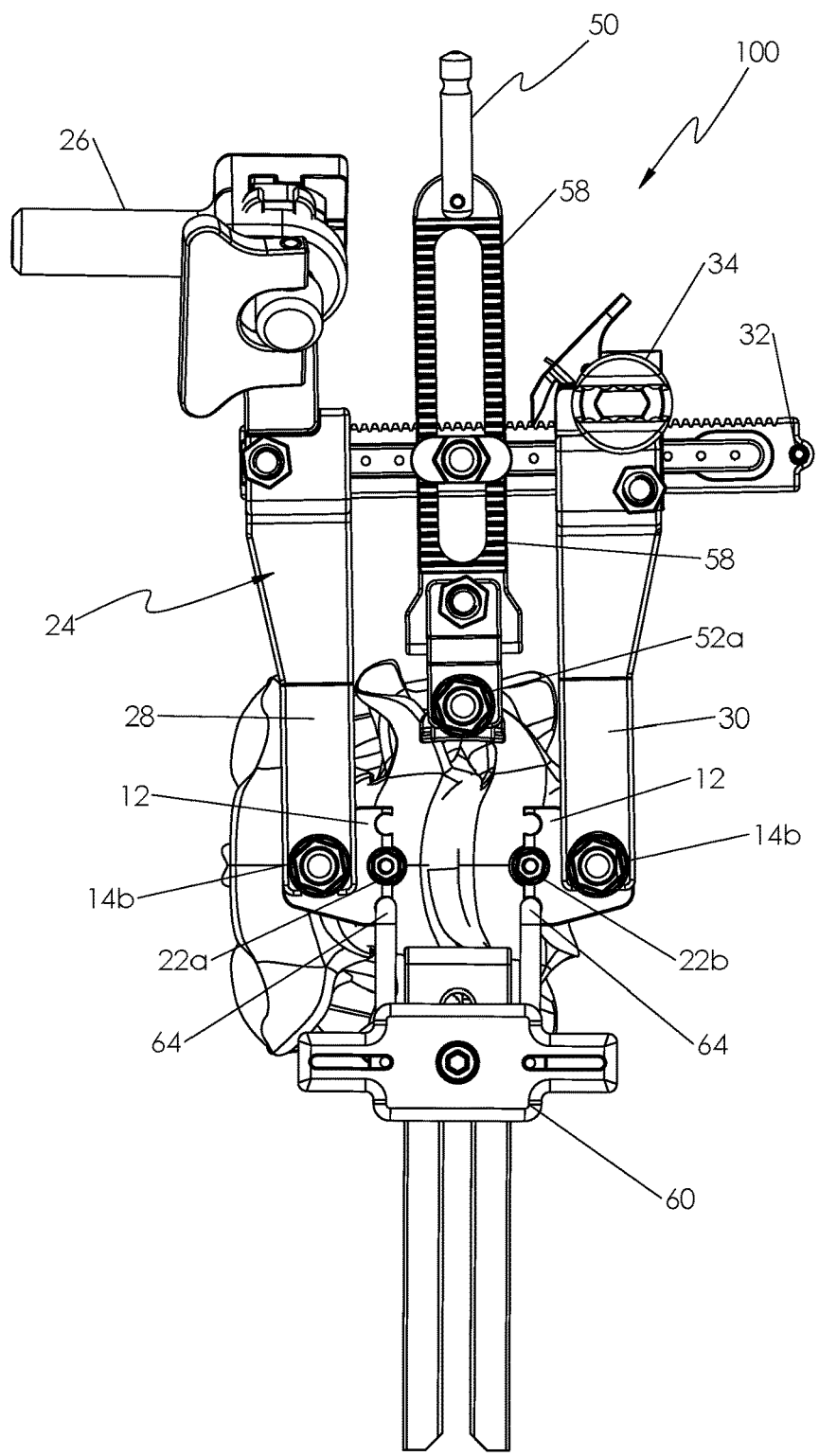
FIG. 1 is a top view of a retractor system in accordance with an embodiment of the present disclosure.

Particular embodiments of the present disclosure will be described herein with reference to the accompanying drawings. As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during proper use. In addition, the term "cephalad" is used in this application to indicate a direction towards a patient's head, whereas the term "caudad" indicates a direction towards the patient's feet. Further still, the term "medial" indicates a direction towards the middle of the body of the patient, while the term "lateral" indicates a direction towards a side of the body of the patient (i.e., away from the middle of the body of the patient). The term "posterior" indicates a direction towards the patient's back, and the term "anterior" indicates a direction towards the patient's front. In the following description, well-known functions or constructions are not described in detail to avoid obscuring the present disclosure in unnecessary detail.

With reference to FIG. 1, an embodiment of the present disclosure is shown generally as a retractor system 100 configured and adapted for a minimally invasive surgical procedure to access, for example, the cervical, thoracic, or lumbar vertebrae. For example, the retractor system 100 may be used in a discectomy for retracting soft tissue and distracting vertebral bodies. The retractor system 100 includes pins 10 (FIG. 2), retractor blades 12, a frame 24, a medial blade 50, and a lateral protector 60.

Figure 4:
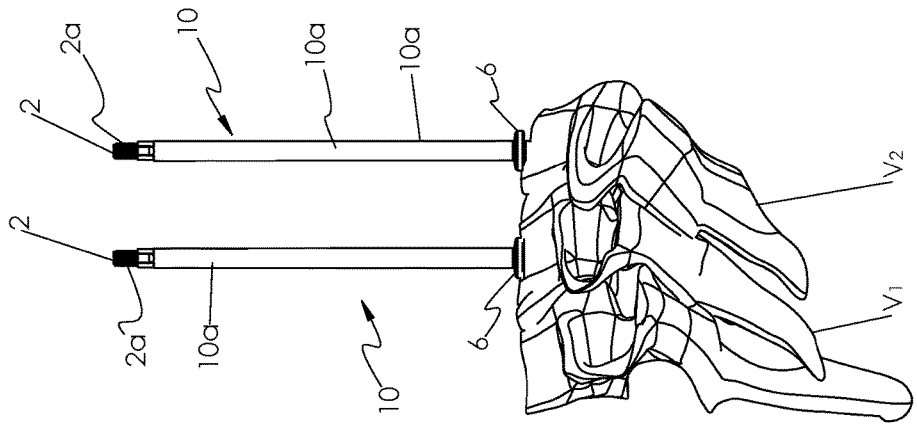
FIGS. 3 and 4 are side views of the pins of FIG. 1 illustrating use with vertebral bodies.
Figure 3:
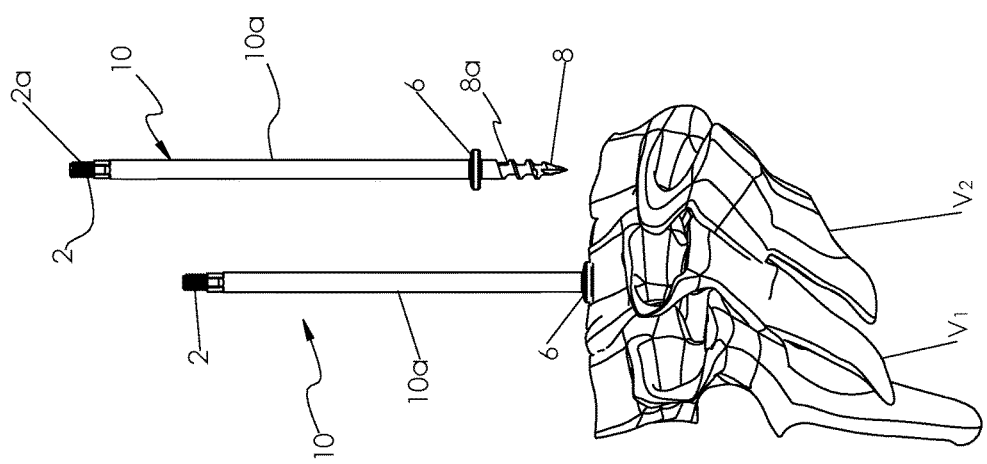
Figure 2:
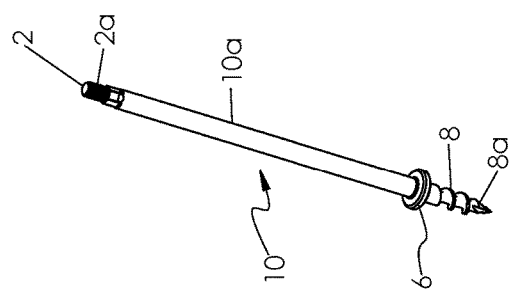
FIG. 2 is perspective view of a pin of the retractor system of FIG. 1.
Figure 5:
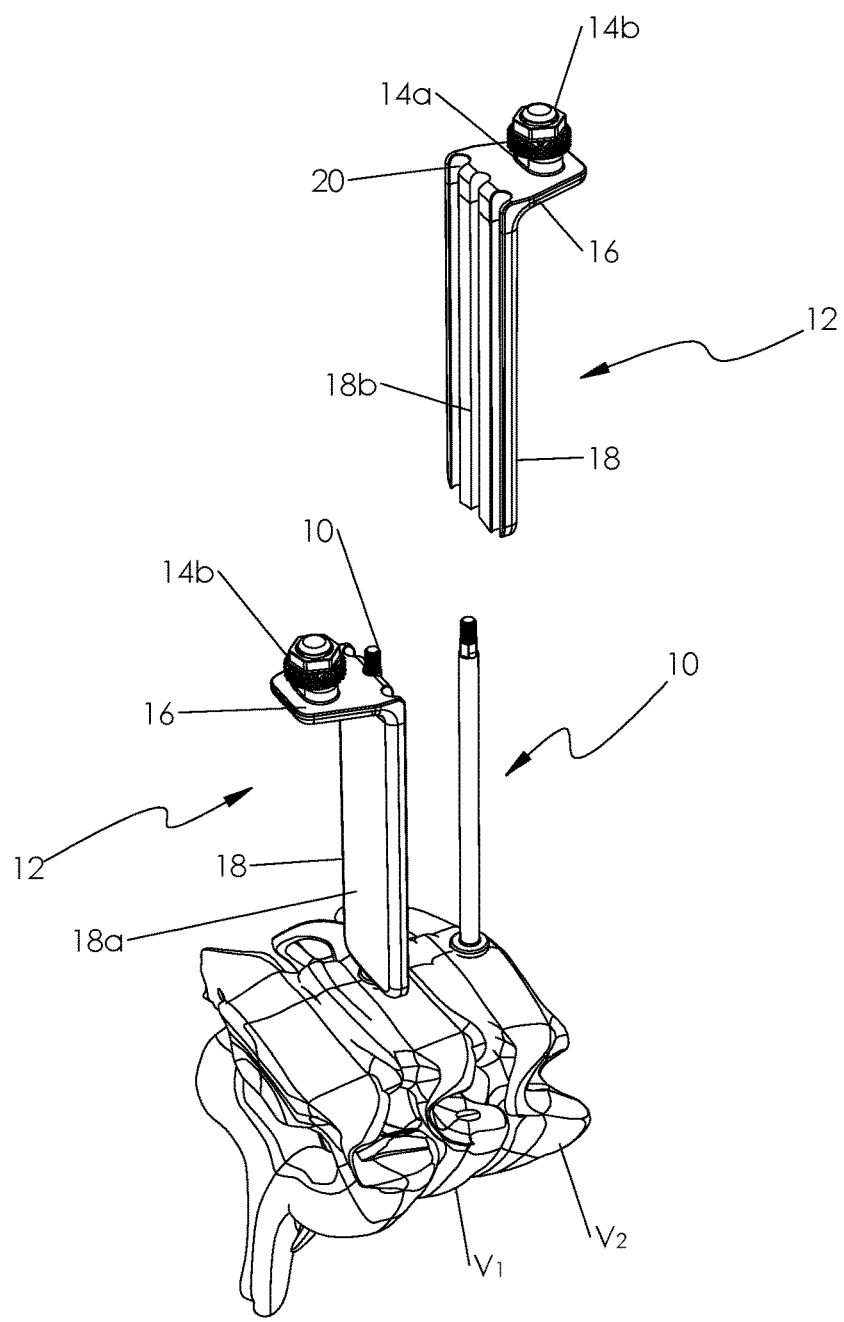
FIG. 5 is a perspective view of the pins and retractor blades of FIG. 1.
Figure 6:
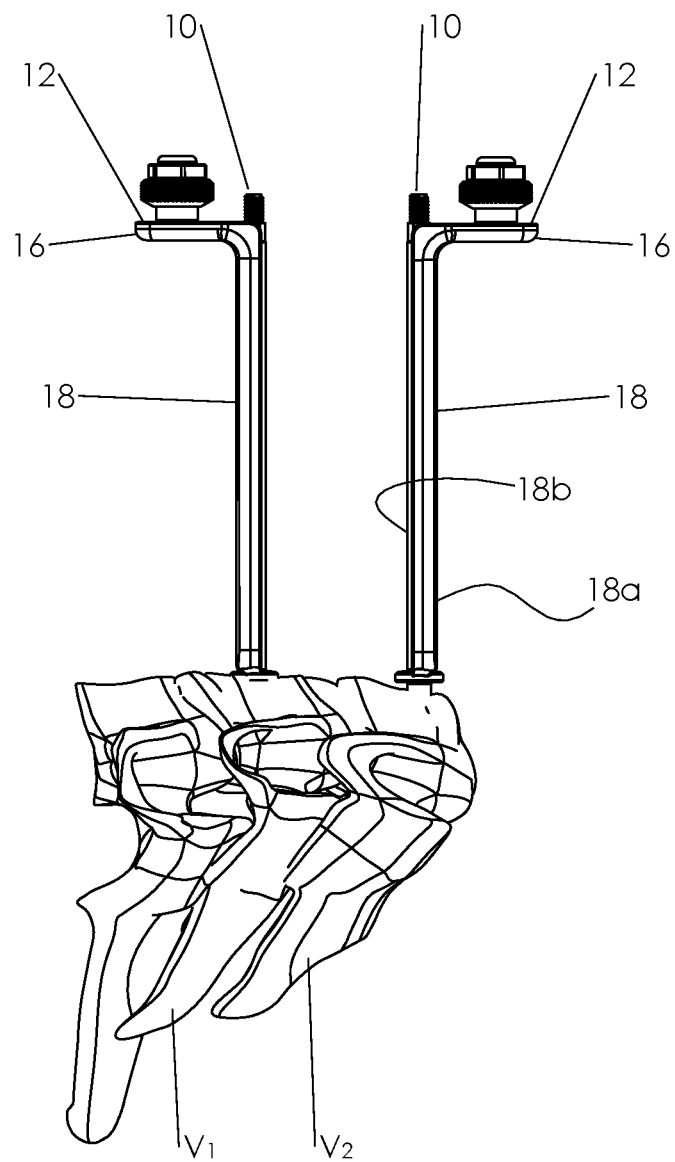
FIGS. 6 and 7 are side views of the pins and retractor blades of FIG. 5, illustrating use with vertebral bodies.
Figure 8:
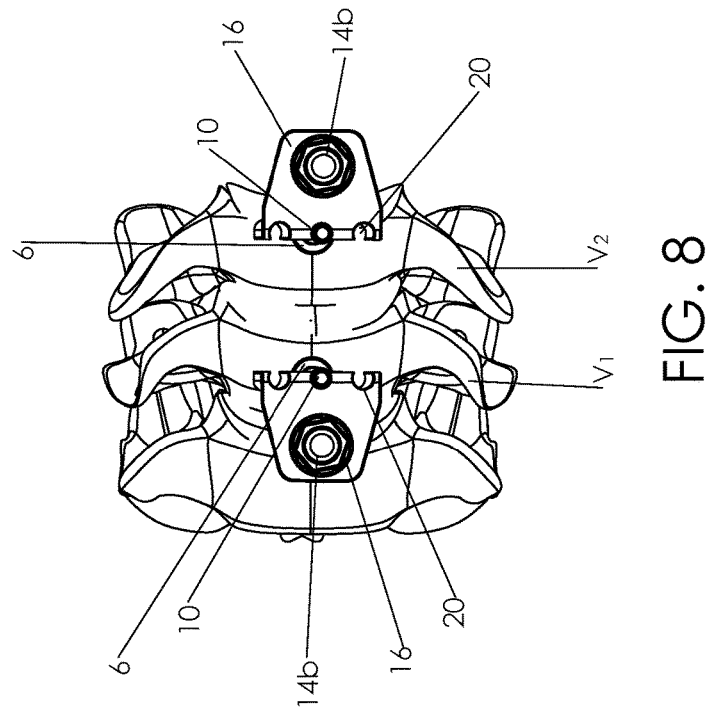
FIG. 8 is a top view of the pins and the retractor blades of FIG. 7.
Figure 7:
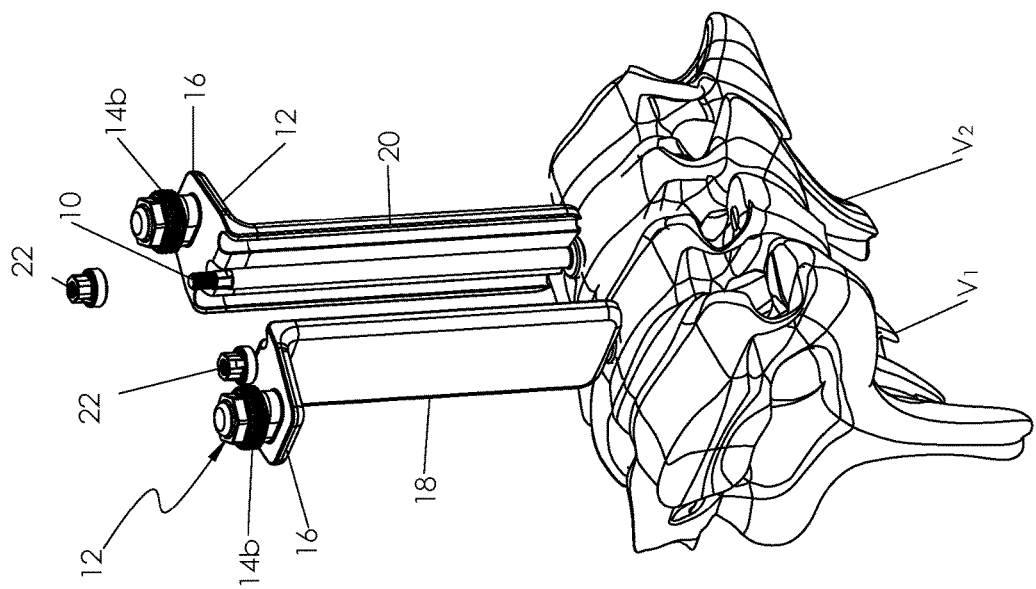

With reference now to FIGS. 2-4, a plurality of pins 10 may be used with the retractor system 100. In particular, the plurality of pins 10 may be used at different levels of the vertebrae. Each pin 10 includes a shaft 10a extending between a first end 2 and a second end 8. In particular, the shaft 10a may be dimensioned to be received in a channel 20 (FIG. 5) defined in the retractor blade 12, as will be discussed. The first end 2 includes a threaded portion 2a configured to threadably engage a cap 22 (FIG. 7) in order to secure the retractor blade 12 with the pin 10, as will be discussed below. The second end 8 is includes a threaded portion 8a configured to penetrate a vertebral body to secure the pin 10 with the vertebral body. In addition, the second end 8 further includes a flange portion 6 disposed proximal of the threaded portion 8a. The flange portion 6 includes a diameter larger than the shaft 10a and the threaded portion 8a in order to limit additional insertion of the pin 10 into the vertebral body once the flange portion 6 engages the vertebral body. Under such a configuration, when the pins 10 are fully inserted in the respective vertebral bodies, i.e., the flange portions 6 engage the respective vertebral bodies, the pins 10 are substantially parallel to each other.

With reference now to FIGS. 5-8, a plurality of retractor blades 12 may be used with the retractor system 100. Each retractor blade 12 includes a coupling portion 16 and a blade portion 18. In an embodiment, the coupling portion 16 and the blade portion 18 may be substantially orthogonal to each other. The coupling portion 16 includes a threaded portion 14a (FIG. 5) and a nut 14b threadably coupled to the threaded portion 14a in order to secure the retractor blade 12 with the frame 24, as will be described below. The blade portion 18 includes opposing first and second surfaces 18a, 18b. The first surface 18a is adapted to engage tissue and the second surface 18b defines a plurality of channels 20. Each channel 20 extends along a length of the blade portion 18. In addition, each 20 channel is dimensioned to receive the pin 10 therein. When the pin 10 is secured with a vertebral body, the retractor blade 12 may be placed in registration with the pin 10. Specifically, the pin 10 may be received in one channel 20 of the plurality of channels 20 defined in the second surface 18b. Under such a configuration, the threaded portion 2a of the first end 2 of the pin 10 extends proximally through a plane defined by the coupling portion 16 of the retractor blade 12 such that the cap 22 may threadably engage the threaded portion 2a of the pin 10 in order to secure the retractor blade 12 with the pin 10. The cap 22 may include an external gripping surface to reduce slippage during rotation.

Figure 9:
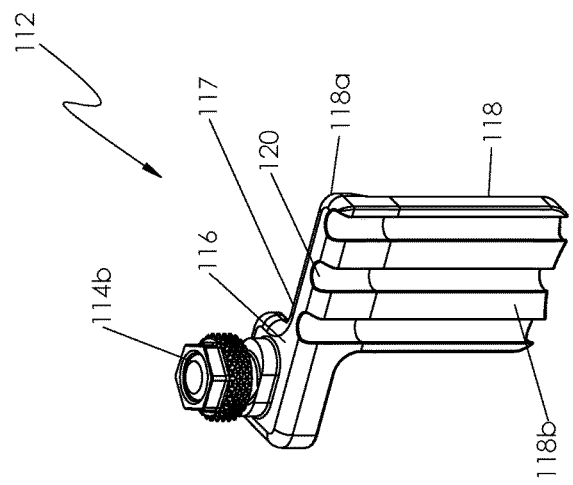
FIG. 9 is a retractor blade for use with the retractor system of FIG. 1 in accordance with another embodiment of the present disclosure.
Figure 10:
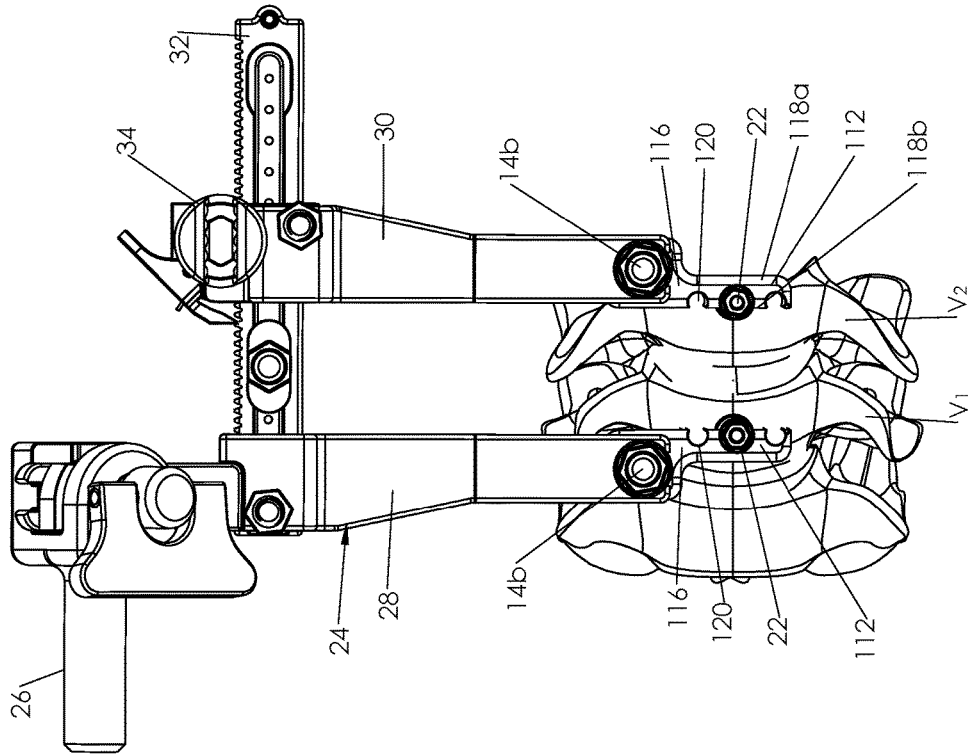
FIG. 10 is a top view of a frame of the retractor system of FIG. 1, illustrating use with the retractor blade of FIG. 9.

With reference now to FIGS. 9 and 10, there is illustrated a retractor blade 112 in accordance with another embodiment of the present disclosure. Retractor blade 112 includes a coupling portion 116 and a blade portion 118. The coupling portion 116 extends transversely from the blade portion 118. However, in contrast to the retractor blade 12 (FIG. 5), the blade portion 118 defines a cutout 117. The placement of the coupling portion 116 and the cutout 117 provides easier access to the vertebral body. As discussed hereinabove with respect to retractor blade 12, the coupling portion 116 includes a threaded portion (not shown) and a nut 114b threadably coupled to the threaded portion in order to secure the retractor blade 112 with the frame 24. In addition, the blade portion 118 includes opposing first and second surfaces 118a, 118b. The first surface 118a is adapted to engage tissue, and the second surface 118b defines a plurality of channels 120. Each channel 120 extends along a length of the blade portion 118 and is dimensioned to receive the pin 10 therein. Under such a configuration, the threaded portion 2a of the first end 2 of the pin 10 extends proximally through a plane defined by the coupling portion 116 of the retractor blade 112 such that the cap 22 may threadably engage the threaded portion 2a of the pin 10 in order to secure the retractor blade 112 with the pin 10.

Figure 11:
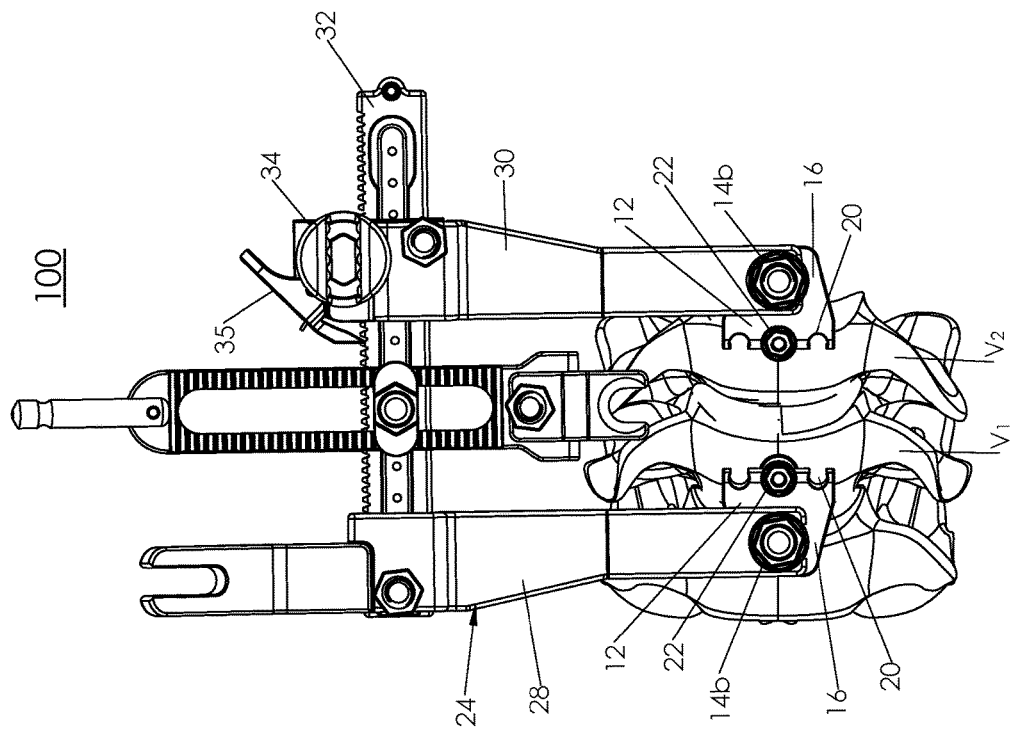
FIGS. 11 and 12 are top views of the frame of the retractor system of FIG. 1 illustrating retraction of vertebral bodies.
Figure 12:
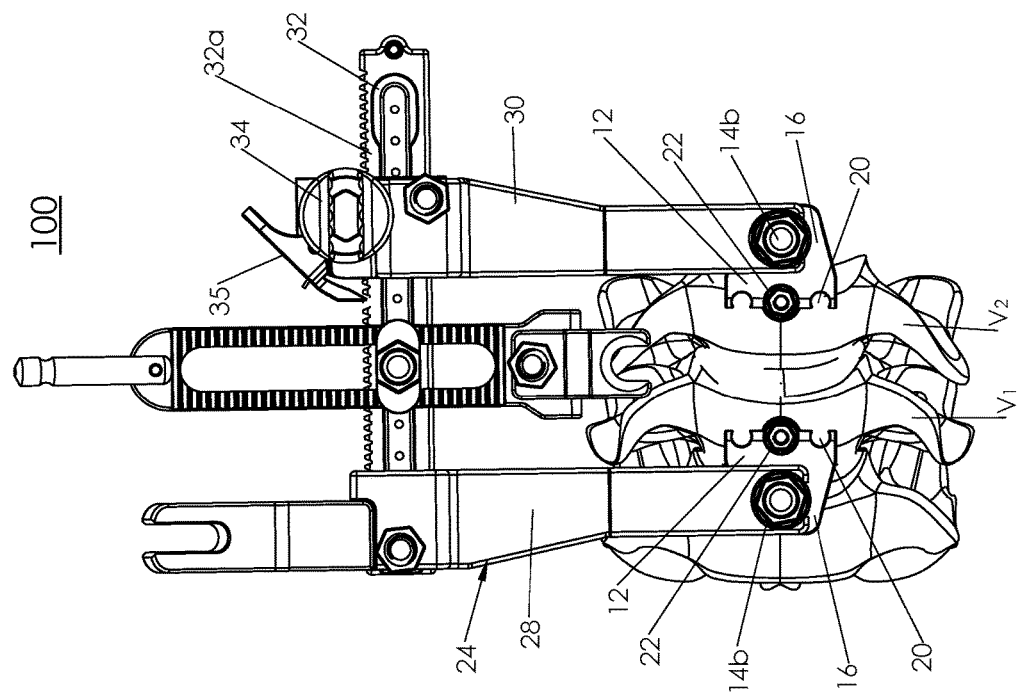
Figure 16:
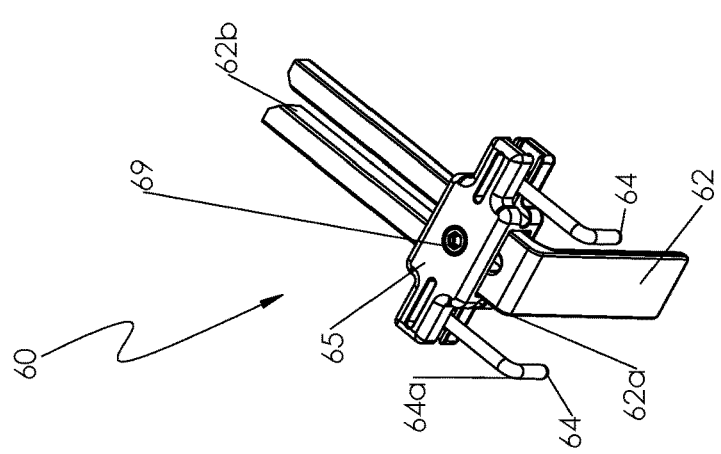
FIG. 16 is a perspective view of a lateral protector for use with the retractor system of FIG. 1.

With reference now to FIGS. 11-12A, the frame 24 is configured to operatively support the retractor blades 12, the medial blade 50 (FIG. 13), and the lateral protector 60 (FIG. 16). With brief reference to FIG. 16, the retraction system 100 further includes a mounting arm 26 configured to attach the frame 24 to a stationary object, such as, e.g., an operating table.

The frame 24 includes a first arm 28, a second arm 30 substantially parallel to the first arm 28, and a third arm 32 operatively supporting the first and second arms 28, 30. In an embodiment, the first arm 28 may be fixedly secured with the third arm 32. The second arm 30 may be movably coupled with the third arm 32 such that the second arm 30 is movable towards and away from the first arm 28. In particular, the second arm 30 includes a knob 34 operatively coupled with the third arm 32 such that rotation of the knob 34 moves the second arm 30 on the third arm 32. For example, the second and third arms 30, 32 may include a rack and pinion configuration. The third arm 32 includes teeth 32a that engage the knob 34. In addition, the second arm 30 further includes a locking pawl 35 that engages the teeth 32a to lock the position of the second arm 30 on the third arm 32. The first and second arms 28, 30 define respective slots (not shown) configured to slidably receive the respective threaded portions 14a (FIG. 5) of the retractors 12. Tightening of the respective nuts 14b secures the first and second arms 28, 30 interposed between the engaging portions 16 of the respective retractor blades 12 and the respective nuts 14b, with the retractor blade 12. Reference may be made to U.S. Pat. No. 8,449,463, the entire contents of which is incorporated herein by reference, for a detailed description of the construction and operation of the frame 24.

With reference now to FIGS. 13-15, the medial blade 50 may be operatively supported on the frame 24 to effect retraction of, e.g., soft tissue, in the transverse direction. The medial blade 50 includes a transverse blade 52 configured to retract, e.g., soft tissue, a securing portion 58, and a handle member 56. The securing portion 58 defines a slot 58a configured to engage a securing member 27 of the frame 24. The securing member 27 releasably secures the securing portion 58 of the medial blade 50 with the frame 24 by a nut 29 threadably engaging the securing member 27. The securing portion 58 of the medial blade 50 includes ridges 58b that engage complementary ridges (not shown) formed on the securing member 27 of the frame 24 to enhance securement of the medial blade 50 with the frame 24 and/or facilitate incremental adjustment of the transverse blade 52 in the transverse direction. By adjusting the nut 29 against the securing member 27 of the frame 24, the transverse position of the transverse blade 52 may be adjusted by the clinician. The transverse blade 52 includes a head portion (not shown) including a threaded portion (not shown) threadably coupled with a nut 52a. The securing portion 58 defines a second slot (not shown) configured to receive the threaded portion of the transverse blade 52 to releasably secure the transverse blade 52 thereto. It is also envisioned that the transverse blade 52 may be directly coupled with the frame 24. For example, the threaded portion of the transverse blade 52 may be received through a slot 32a defined in third arm 32 and the nut 52a may threadably engage the threaded portion to directly secure the transverse blade 52 to the frame 24. The handle member 56 extends from the securing portion 58. The handle member 56 is releasably coupled with the securing portion 58.

Figure 18:
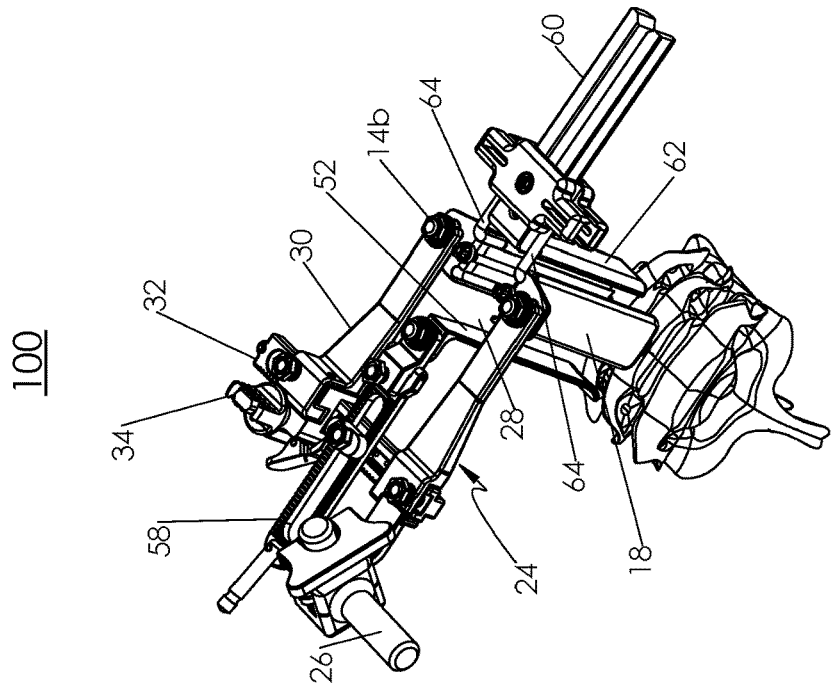
FIG. 18 is a perspective view of the retractor system of FIG. 17.
Figure 17:
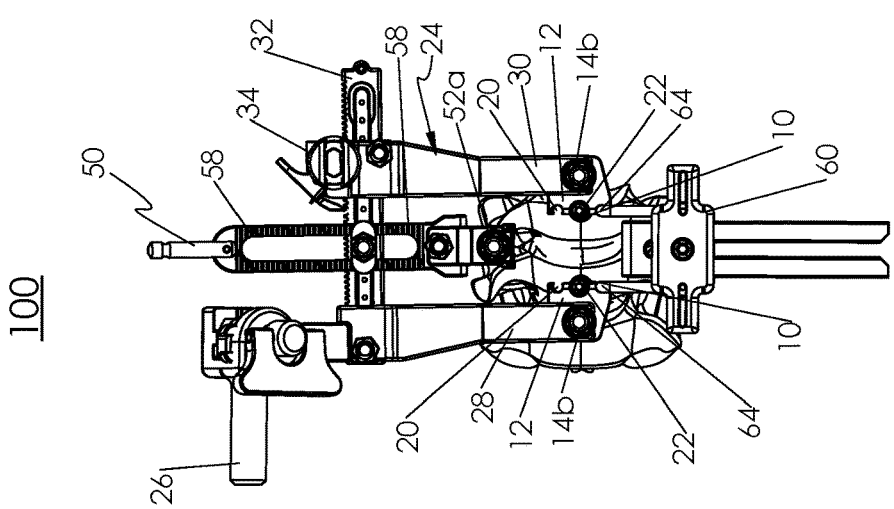
FIG. 17 is a perspective view of the retractor system of FIG. 1 illustrating use with the lateral protector of FIG. 16.

With reference now to FIGS. 16-18, the lateral protector 60 is configured to be attached to at least one retractor blade 12. The lateral protector 60 includes a blade member 62, a pair of prongs 64, and a coupling member 65 coupling the prongs 64 with the blade member 62. In particular, the blade member 62 defines a head portion 62a defining a slot 62b configured to receive a screw 69 to adjustably secure a relative position of the blade member 62 with respect to the coupling member 65. The pair of prongs 64 are also secured with the coupling member 65. Each prong 64 has an L-shape and includes an engaging portion 64a configured to be received in the channel 20 defined in the retractor blade 12. Under such a configuration, the prongs 64 may be received in the respective channels 20 of opposing retractor blades 12 or, alternatively, the respective channels 120 of opposing retractor blades 112. While the prongs 64 are stationary with the retractor blades 12, the transverse position of the blade member 62 may be adjustable by the clinician. The blade member 62 is configured to retract, e.g., soft tissue, in the transverse direction. In this manner, the blade member 62 and the transverse blade 52 (FIG. 13) of the medial blade 50 may retract tissue in opposite transverse directions.

Figure 19:
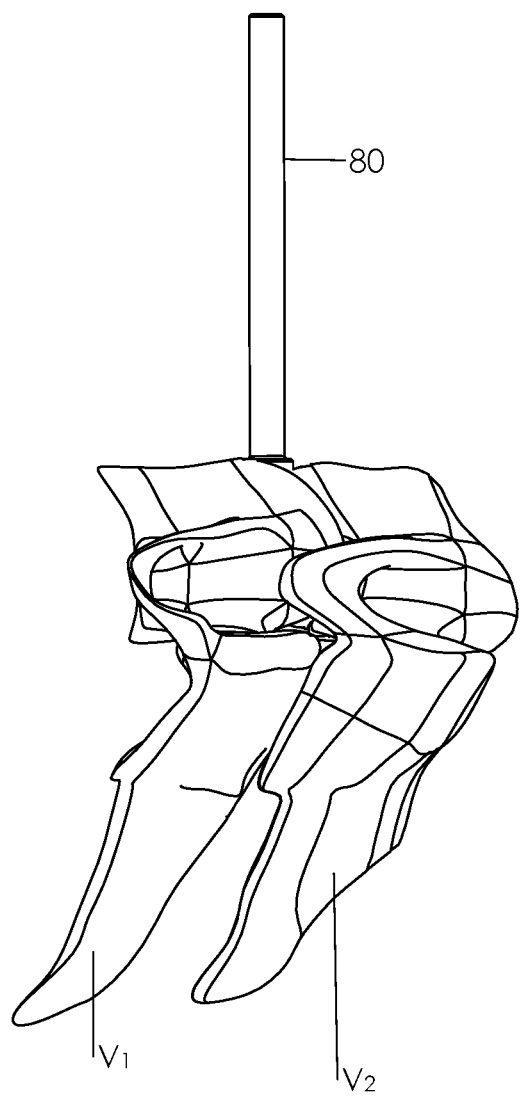
FIG. 19 is a side view of an indicator pin for use with the retractor system of FIG. 1.
Figure 20:
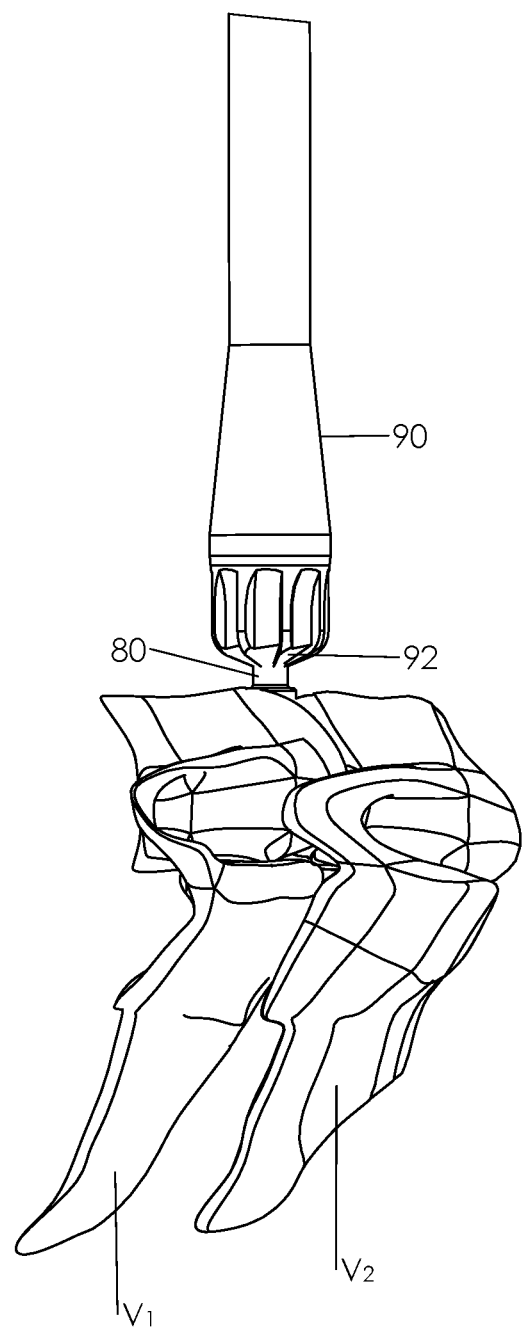
FIG. 20 is a side view of a reamer for use with the retractor system of FIG. 1.
Figure 21:
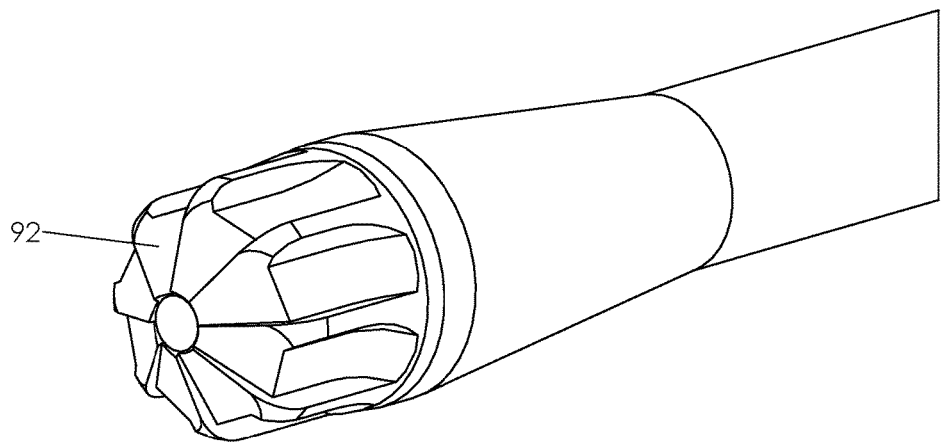
FIG. 21 is a partially enlarged perspective view of the reamer of FIG. 20.

With reference now to FIG. 19, initially the clinician locates the center of a vertebral disc space and inserts an indicator pin 80 thereto. The indicator pin 80 may serve as a center point in a medial-lateral direction and in the cephalad-caudal direction. With reference now to FIGS. 20 and 21, a reamer 90 may be utilized to remove any osteophytes from, e.g., an anterior surface, of the vertebral body $V_1$, $V_2$. Specifically, the reamer 90 is inserted over the indicator pin 80. The reamer 90 includes a cutting surface 92 at a distal end thereof. Once the osteophytes have been removed, the reamer 90 can be removed from the indicator pin 80.

Figure 22:
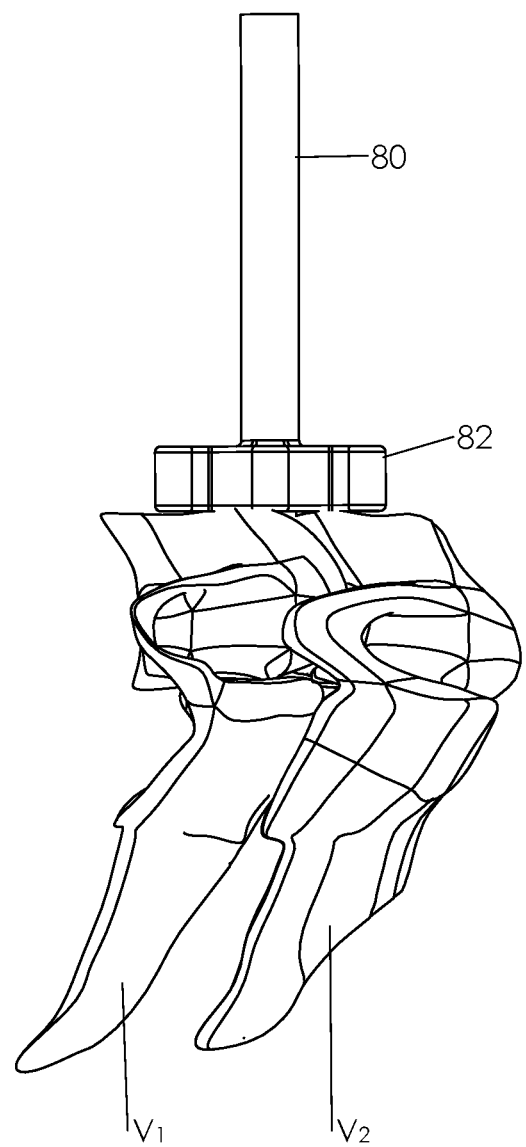
FIG. 22 is a side view of a drill guide for use with the retractor system of FIG. 1, illustrating use with the indicator pin of FIG. 19.
Figure 24:
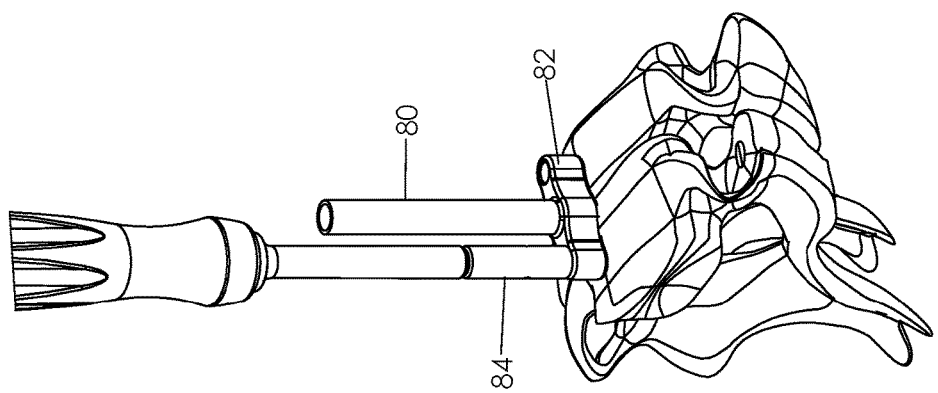
FIG. 24 is a perspective view of a drill for use with the retractor system of FIG. 1, illustrating use with the drill guide and the indicator pin of FIG. 22.
Figure 23:
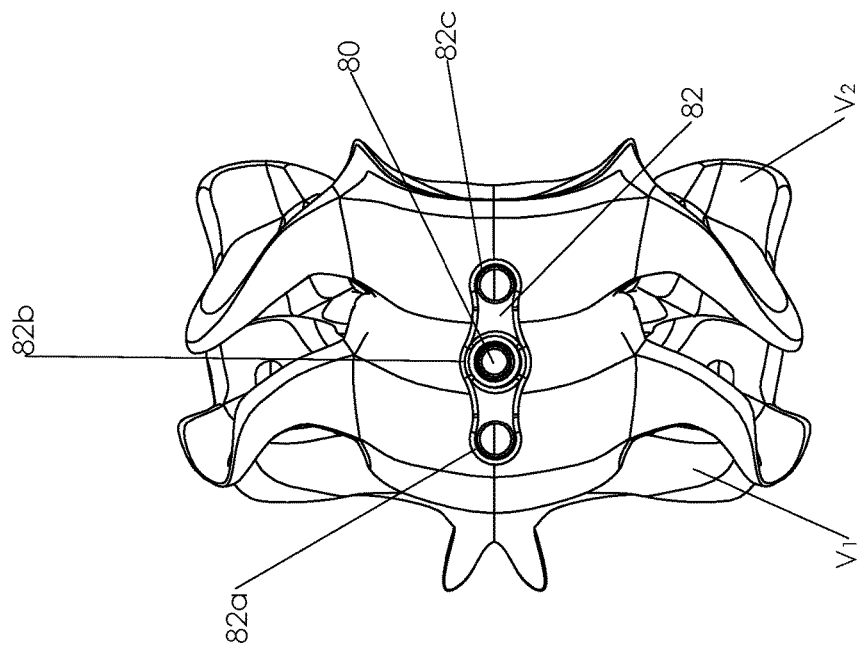
FIG. 23 is a top view of the drill guide and the indicator pin of FIG. 22, illustrating use with vertebral bodies.

With reference now to FIG. 22-24, a drill guide 82 may be utilized to locate insertion points for the pins 10. Specifically, the drill guide 82 is inserted through the indicator pin 80 such that the drill guide 82 is in registration with the vertebral bodies $V_1$, $V_2$. In particular, the drill guide 82 defines bores 82a, 82b, 82c. The indicator pin 80 is received through the bore 82b and the bores 82a, 82c are in registration with the respective vertebral bodies $V_1$, $V_2$. At this time, a drill 84 can be utilized to form holes in the vertebral bodies $V_1$, $V_2$ to receive the respective pins 10. The pins 10 are inserted into the vertebral bodies $V_1$, $V_2$ by an amount determined by the flange portion 6. The flange portion 6 having a wider base than the second end 8 of the pin 10 ensures that the pins 10 inserted into the respective vertebral bodies $V_1$, $V_2$ are substantially parallel to each other.

With reference back to FIGS. 5 and 6, a first retractor blade 12 can be inserted over the pin 10 secured with the vertebral body $V_1$, and a second retractor blade 12 can be inserted over the pin 10 secured with the vertebral body $V_2$. Specifically, the clinician can align and slide the retractor blades 12 along the length of the respective pins 10 through the respective channels 20. Caps 22 can be utilized to secure the retractor blades 12 with the respective pins 10.

With reference now to FIG. 11, at this time, the frame 24 may be attached to the retractor blades 12 secured with the vertebral bodies $V_1$, $V_2$ by inserting the threaded portions 14a (FIG. 5) of the retractor blades 12 in the respective slots (not shown) of the first and second arms 28, 30 and tightening the nuts 14b. Upon securing the retractor blades 12 with the frame 24, the knob 34 of the frame 24 may be rotated to displace the second arm 30 away from the first arm 28. In this manner, the clinician can distract the vertebral bodies $V_1$, $V_2$, as shown in FIG. 12.

With brief reference back to FIGS. 14 and 15, the medial blade 50 may also be attached to the frame 24 in order to retract soft tissue in the area around the retractor blades 12. In addition, the lateral protector 60 may also be attached to the retractor blades 12 in order to further secure the retractor blades 12 and retract soft tissue in the area around the retractor blades 12.

Figure 25:
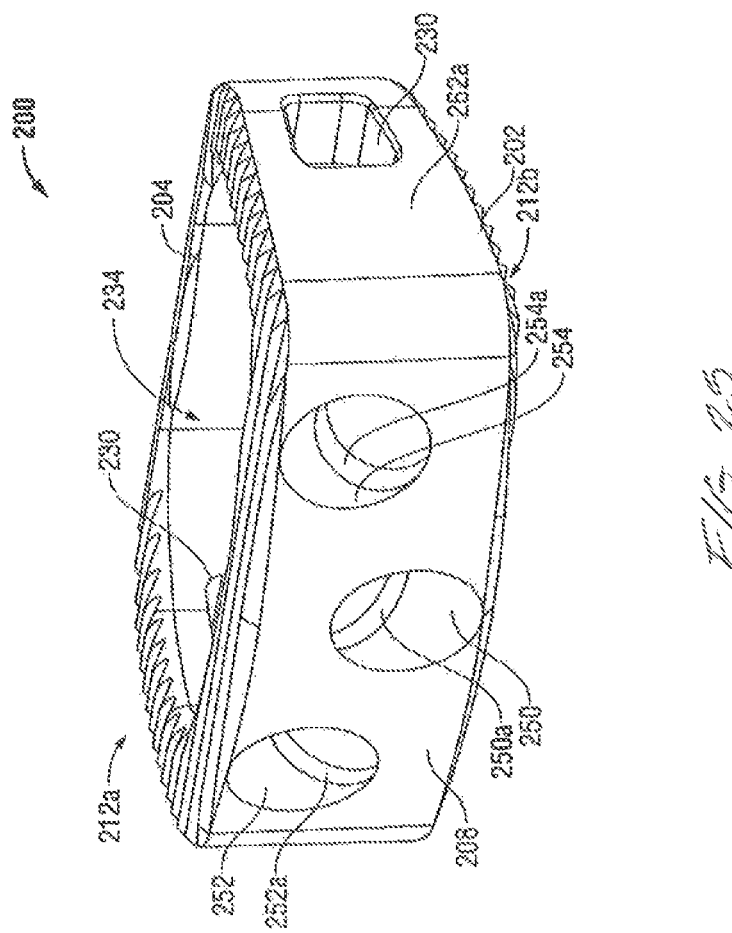
FIG. 25 is a perspective view of an implant device for use with the retractor system of FIG. 1.

At this time, the disc space can be cleared using standard techniques. With reference to FIG. 25, an implant device 200 can then be inserted into the cleared disc space. The implant device 200 includes a body 202 extending between a first end surface 204 and a second end surface 208 to define respective top and bottom vertebral engaging surfaces 212a, 212b, as well as opposed side surfaces 262a. The body 202 defines an aperture 230 through the side surfaces 262a. The body 202 defines a hollow central region 234. The body 202 further defines a plurality of angled apertures 250, 252, 254 disposed through the second end surface 208. Each angled aperture 250, 252, 254 is adapted to receive a bone screw (not shown) therethrough for insertion into the vertebral bodies $V_1$, $V_2$. As the bone screws are advanced through the respective apertures 250, 252, 254, the bone screws threadingly engage respective lips 250a, 252a, 254a to retain the bone screws within the respective apertures 250, 252, 254. Reference may be made to U.S. Pat. No. 9,017,409, the entire contents of which is incorporated herein by reference, for a detailed description of the construction and operation of the implant device 200.

Upon inserting the implant device 200 into the cleared disc space, the knob 34 may be rotated in an opposite direction to move the second arm 30 towards the first arm 28 until the vertebral bodies $V_1$, $V_2$ engage the implanted device. It is also contemplated that, e.g., a cervical plate, may be utilized to inhibit additional movement of the vertebral bodies $V_1$, $V_2$.

Upon completing the desired surgical procedure, the clinician may adjust the retractor blades 12 to perform surgical procedures on other vertebral bodies in a manner described hereinabove. For example, the frame 24 may be detached from one of the retractor blades 12 by adjusting one of the nuts 14b. The pin 10, the cap 22, and the retractor blade 12 associated with the vertebral body $V_2$ may be removed. With the pin 10 and its associated cap 22 still secured to the vertebral body $V_1$, the retractor blade 12 can be rotated 180 degrees about the pin 10. A third pin 10, a third retractor blade 12, and a third cap 22 can then be inserted into a third vertebral body located adjacent the vertebral body $V_1$, on the side opposite of the vertebral body $V_1$. The frame 24 can be attached to the retractor blades 12 using the nuts 14b on the respective retractor blades 12. In this manner, the vertebral body $V_1$ can then be distracted from the third vertebral body. At this time, surgical procedures may be carried out such as, e.g., clearing the disc space, implanting a device or installing a device. Upon completion of the surgical procedures, the retractor system 100 may be removed from the surgical site.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A method of distracting adjacent vertebral bodies comprising:
   inserting a first pin into a first vertebral body;
   inserting a second pin into a second vertebral body adjacent the first vertebral body;
   positioning a first retractor blade over the first pin;
   positioning a second retractor blade over the second pin;
   attaching a first arm of a frame to the first retractor blade and a second arm of the frame to the second retractor blade;
   displacing the second arm of the frame away from the first arm to distract the first and second vertebral bodies;
   inserting prongs of a lateral protector into respective channels defined in the first and second retractor blades; and
   retracting tissue by a transverse blade of the lateral protector.

2. The method according to claim 1, further comprising inserting an indicator pin in the center of a vertebral disc space.

3. The method according to claim 2, wherein inserting the indicator pin includes inserting the indicator pin in the center point in a medial-lateral direction.

4. The method according to claim 2, wherein inserting the indicator pin includes inserting the indicator pin at the center point in a cephalad-caudal direction.

5. The method according to claim 2, further comprising inserting a reamer over the indicator pin to remove osteophytes from the vertebral body using a cutting surface at a distal end of the reamer.

6. The method according to claim 2, further comprising inserting a drill guide through the indicator pin such that the drill guide is in registration with the first and second vertebral bodies.

7. The method according to claim 6, further comprising drilling holes in the first and second vertebral bodies through first and second bores of the drill guide in registration with the first and second vertebral bodies.

8. The method according to claim 1, wherein positioning the first retractor blade over the first pin includes sliding the first pin through a longitudinal channel defined in the first retractor blade.

9. The method according to claim 1, further comprising clearing a disc space located between the first and second vertebral bodies.

10. The method according to claim 9, further comprising implanting a device into the cleared disc space.

11. The method according to claim 9, further comprising displacing the second arm of the frame towards the first arm such that the first and second vertebral bodies engage the device disposed in the cleared disc space.

12. The method according to claim 1, further comprising attaching a medial blade to the frame to retract tissue in the area around the first and second retractor blades.

13. The method according to claim 1, further comprising detaching the second arm of the frame from the second retractor.

14. The method according to claim 13, further comprising inserting a third pin into a third vertebral body adjacent the first vertebral body.

15. The method according to claim 14, further comprising rotating the first retractor blade about 180 degrees about the first pin.

16. The method according to claim 15, further comprising attaching the second retractor blade over the third pin and attaching the second arm of the frame to the second retractor blade.

17. The method according to claim 16, further comprising displacing the second arm of the frame away from the first arm to distract the first and third vertebral bodies.

18. The method according to claim 17, further comprising clearing a disc space located between the first and third vertebral bodies.

19. The method according to claim 18, further comprising implanting a device into the cleared disc space between the first and third vertebral bodies.

20. The method according to claim 19, further comprising displacing the second arm of the frame towards the first arm such that the first and third vertebral bodies engage the device disposed in the cleared disc space between the first and third vertebral bodies.

21. The method according to claim 1, further comprising disengaging the prongs of the lateral protector from the first and second retractor blades.

22. A method of distracting adjacent vertebral bodies comprising:
    inserting first and second pins into respective first and second vertebral bodies;
    positioning first and second retractor blades of a retractor system over the respective first and second pins, the retractor system including:
        a frame including a first arm, a second arm movable relative to the first arm, and a third arm operatively supporting the first and second arms, the first and second retractor blades coupled to the respective first and second arms of the frame; and
        a lateral protector including prongs configured to be received in respective channels defined in the first and second retractor blades, and a transverse blade;
    displacing the second arm of the frame away from the first arm to distract the first and second vertebral bodies;
    inserting the prongs of the lateral protector into the respective channels of the first and second retractor blades; and
    retracting tissue by the transverse blade of the lateral protector.

23. The method according to claim 22, further comprising clearing a disc space located between the first and second vertebral bodies.

24. The method according to claim 23, further comprising implanting a device into the cleared disc space.

25. The method according to claim 24, further comprising displacing the second arm of the frame towards the first arm such that the first and third vertebral bodies engage the device disposed in the cleared disc space between the first and third vertebral bodies.

26. The method according to claim 22, further comprising detaching the second arm of the frame from the second retractor.

27. The method according to claim 22, further comprising inserting a third pin into a third vertebral body adjacent the first vertebral body.

28. The method according to claim 27, further comprising attaching the second retractor blade over the third pin and attaching the second arm of the frame to the second retractor blade.

29. The method according to claim 28, further comprising displacing the second arm of the frame away from the first arm to distract the first and third vertebral bodies.

30. The method according to claim 22, further comprising rotating the first retractor blade about 180 degrees about the first pin.

* * * * *